(12) United States Patent
Bachmann et al.

(10) Patent No.: US 6,413,926 B2
(45) Date of Patent: Jul. 2, 2002

(54) PROCESS FOR TREATING TEXTILE MATERIALS

(75) Inventors: Frank Bachmann, Freiburg (DE); Josef Dannacher, Basel (CH); Cornelia Makowka, Laufenburg (DE); Gunther Schlingloff, Riehen; Peter Weingartner, Diegten, both of (CH); Grit Richter, Neuenburg (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/835,245

(22) Filed: Apr. 13, 2001

Related U.S. Application Data

(63) Continuation of application No. 09/283,546, filed on Apr. 1, 1999, now abandoned.

(30) Foreign Application Priority Data

Apr. 6, 1998 (EP) .............................................. 98810289

(51) Int. Cl.[7] .............................. C11D 7/26; C11D 7/32; C11D 7/38

(52) U.S. Cl. ...................... 510/311; 510/372; 510/376; 252/186.33; 502/167; 502/200; 502/324

(58) Field of Search ................................. 510/311, 372, 510/376; 8/137; 252/186.33; 502/167, 200, 324

(56) References Cited

U.S. PATENT DOCUMENTS 5,733,341 A * 3/1998 Eckhardt et al. ................. 8/111

FOREIGN PATENT DOCUMENTS

| DE | 19529905 | * | 2/1997 |
| EP | 0587552 | | 3/1994 |
| EP | 630964 | * | 12/1994 |
| EP | 717103 | * | 6/1996 |
| WO | WO 97/07192 | * | 2/1997 |

* cited by examiner

*Primary Examiner*—Gregory Del Cotto
(74) *Attorney, Agent, or Firm*—Kevin T. Mansfield

(57) ABSTRACT

A process for preventing the redeposition of migrant dyes in a washing liquor by adding to each liter of the washing liquor, which comprises a peroxide-containing detergent, from 0.5 to 150 mg of one or more asymmetric manganese complexes of the salen type.

13 Claims, No Drawings

PROCESS FOR TREATING TEXTILE MATERIALS

This is a continuation of application Ser. No. 09/283,546, now abandoned, filed on Apr. 1, 1999.

The present invention relates to a process for preventing the redeposition of migrating dyes in wash liquors comprising a peroxide and a manganese catalyst, to manganese catalysts suitable for the process, and to detergent formulations comprising these catalysts.

It is already known that some manganese complexes of the salen type are suitable catalysts for oxidations with peroxygen compounds, especially as part of a washing process. The salen complexes involved are exclusively symmetrical. It has also been described before that certain other manganese complexes possess a pronounced bleaching effect on dirt and dyes in wash liquors.

It has now been found that certain asymmetric manganese complexes of the salen type exhibit a much greater specific action as catalysts for preventing the redispositon of migrating dyes in wash liquors without notably damaging either dye or fibre. Complexes are termed asymmetric when they come about through the reaction of 2 mol of two differently modified salicylaldehydes or o-hydroxyphenyl ketones with 1 mol of ethylenediamine or another modified diamine building block and so possess two differently substituted aromatic radicals.

The present invention therefore provides a process for preventing the redeposition of migrating dyes in a wash liquor, which comprises adding to the wash liquor, which comprises a peroxide-containing detergent, from 0.5 to 150 mg, preferably from 1.5 to 75 mg and, in particular, from 7.5 to 40 mg per liter of wash liquor of one or more compounds of the formula

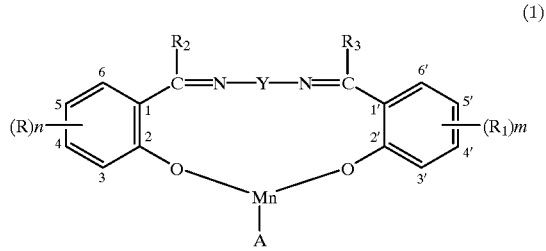

(1)

in which n is 0, 1, 2 or 3, m is 1, 2 or 3,

A is an anion;

Y is a linear or branched alkylene radical of the formula
—[C($R_5$)$_2$]$_r$—, where r is an integer from 1 to 8 and the $R_5$ radicals independently of one another are hydrogen or $C_1$–$C_4$alkyl;

—CX=CX—, in which X is cyano, linear or branched $C_1$–$C_8$alkyl or di(linear or branched $C_1$–$C_8$alkyl)-amino, —(CH$_2$)$_q$—NR$_4$—(CH$_2$)$_q$—, in which $R_4$ is hydrogen or linear or branched $C_1$–$C_4$alkyl and q is 1, 2, 3 or 4; or a 1,2-cyclohexylene radical of the formula:

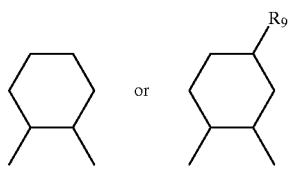

or a 1,2-aryl radical of the formula

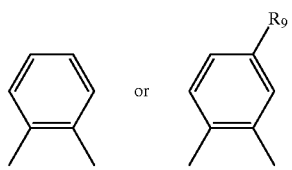

in which
$R_9$ is $SO_3H$, $CH_2OH$ or $CH_2NH_2$,
R and $R_1$ independently of one another are cyano, halogen, $OR_5$ or $COOR_5$, in which $R_5$ is hydrogen or linear or branched $C_1$–$C_4$alkyl, or are nitro, linear or branched $C_1$–$C_8$alkyl, linear or branched, partially fluorinated or perfluorinated $C_1$–$C_8$alkyl, $NHR_6$ or $NR_6R_7$ in which $R_6$ and $R_7$ are identical or different and are each linear or branched $C_1$–$C_{12}$alkyl or in which $R_6$ and $R_7$, together with the nitrogen atom connecting them, form a 5-, 6- or 7-membered ring which may include further heteroatoms, or are linear or branched $C_1$–$C_8$alkyl-$R_8$, in which $R_8$ is a radical $OR_5$, $COOR_5$ or $NR_6R_7$ with the above definitions or is $NH_2$, or are —$N^{\oplus}R_4R_6R_7$, in which $R_4$, $R_6$ and $R_7$ are as defined above, $R_2$ and $R_3$ independently of one another are hydrogen, linear or branched $C_1$–$C_4$ alkyl or unsubstituted aryl, or aryl substituted by cyano, halogen, $OR_5$ or $COOR_5$, in which $R_5$ is hydrogen or linear or branched $C_1$–$C_4$alkyl, or by nitro, linear or branched $C_1$–$C_8$alkyl, $NHR_6$ or $NR_6R_7$ in which $R_6$ and $R_7$ are identical or different and are as defined above, or by linear or branched $C_1$–$C_8$alkyl-$R_8$, in which $R_8$ is a radical $OR_5$, $COOR_5$ or $NR_6R_7$ with the above definitions or is $NH_2$, or by —$N^{\oplus}R_4R_6R_7$, in which $R_4$, $R_6$ and $R_7$ are as defined above, with the proviso that R and $R_1$ do not have the same definition if n and m are identical.

In the compounds of the formula (1) in which n is 2 or 3 the radicals R can have the same or different definitions. With respect to the radicals $R_1$ the same applies to compounds of the formula (1) in which m is 2 or 3.

Where Y is a 1,2-cyclohexylene radical it may be present in each of its stereoisomeric cis/trans forms.

Preferably Y is a radical of the formula —(CH$_2$)$_r$—, where r is an integer from 1 to 8, or of the formula —C($R_5$)$_2$—(CH$_2$)$_p$—C($R_5$)$_2$— in which p is a number from 0 to 6 and $R_5$ is hydrogen or $C_1$–$C_4$alkyl.

In particularly preferred compounds of the formula (1) Y is a radical of the formula —(CH$_2$)$_r$—, where r is an integer from 1 to 4, or of the formula —(CR$_5$)$_2$—(CR$_5$)$_2$—, in which $R_5$ independently at each occurrence is hydrogen or methyl.

Halogen is preferably chlorine, bromine or fluorine, with particular preference being given to chlorine.

If n or m is 1 the groups R and $R_1$ are preferably in position 4 of the respective benzene ring except when R or $R_1$, respectively, is nitro or $COOR_5$. In this case the group R or $R_1$, respectively, is preferably in position 5.

If n or m is 2 the two R groups or $R_1$ groups are preferably in positions 4 and 6 of the respective benzene ring except when R or $R_1$, respectively, is nitro or $COOR_5$. In this case the two R groups or $R_1$ groups, respectively, are preferably in positions 3 and 5.

If R or $R_1$ is di($C_1$–$C_{12}$alkyl)amino the alkyl group can be straight-chain or branched. It preferably contains from 1 to 8, in particular from 1 to 4 and, especially, 1 or 2 carbon atoms.

The radicals R and $R_1$ are preferably hydrogen, nitro, $OR_5$, $COOR_5$ or $N(R_5)_2$, with $R_5$ being hydrogen or $C_1$–$C_4$alkyl, especially methyl or ethyl.

The radicals $R_2$ and $R_3$ are especially hydrogen, methyl, ethyl or unsubstituted phenyl.

Aryl is, for example, naphthyl or especially phenyl.

If $R_6$ and $R_7$ together with the nitrogen atom connecting them form a 5-, 6- or 7-membered ring this ring is especially a pyrrolidine, piperidine, morpholine or piperazine ring. The piperazine ring can be substituted, by alkyl, for example, on the nitrogen atom that is not joined to the phenyl radical.

Examples of suitable anions are halide, such as chloride, perchlorate, sulfate, nitrate, hydroxide, $BF_4^-$, $PF_6^-$, carboxylate, acetate, tosylate and triflate. Preference among these is given to chloride, acetate and carboxylate.

The present invention also provides the compounds of the formula

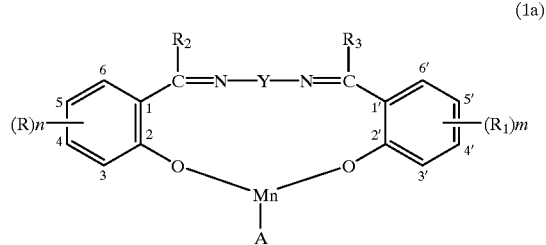

(1a)

in which n is 0, 1, 2 or 3, m is 1, 2 or 3,

A is an anion;

Y is a linear or branched alkylene radical of the formula
—[C($R_5$)$_2$]$_r$—, where r is an integer from 1 to 8 and the $R_5$ radicals independently of one another are hydrogen or $C_1$–$C_4$alkyl;

—CX═CX—, in which X is cyano, linear or branched $C_1$–$C_8$alkyl or di(linear or branched $C_1$–$C_8$alkyl)-amino, —(CH$_2$)$_q$—NR$_4$—(CH$_2$)$_q$—, in which $R_4$ is as defined above and q is 1, 2, 3 or 4; or a 1,2-cyclohexylene radical of the formula:

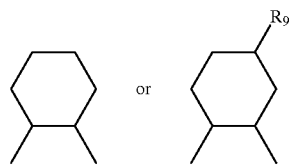

or a 1,2-aryl radical of the formula

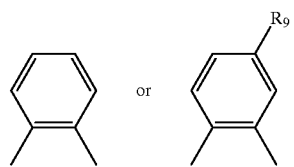

in which $R_9$ is $SO_3H$, $CH_2OH$ or $CH_2NH_2$,

R and $R_1$ independently of one another are cyano, halogen, $OR_5$ or $COOR_5$, in which $R_5$ is hydrogen or linear or branched $C_1$–$C_4$alkyl, or are nitro, linear or branched $C_1$–$C_8$alkyl, linear or branched, partially fluorinated or perfluorinated $C_1$–$C_8$alkyl, $NHR_6$ or $NR_6R_7$ in which $R_6$ and $R_7$ are identical or different and are each linear or branched $C_1$–$C_{12}$alkyl or in which $R_6$ and $R_7$, together with the nitrogen atom connecting them, form a 5-, 6- or 7-membered ring which may include further heteroatoms, or are linear or branched $C_1$–$C_8$alkyl-$R_8$, in which $R_8$ is a radical $OR_5$, $COOR_5$ or $NR_6R_7$ with the above definitions or is $NH_2$, or are —N$^\oplus$$R_4R_6R_7$, in which $R_4$, $R_6$ and $R_7$ are as defined above, $R_2$ and $R_3$ independently of one another are hydrogen, linear or branched $C_1$–$C_4$ alkyl or unsubstituted aryl, or aryl substituted by cyano, halogen, $OR_5$ or $COOR_5$, in which $R_5$ is hydrogen or linear or branched $C_1$–$C_4$alkyl, or by nitro, linear or branched $C_1$–$C_8$alkyl, $NHR_6$ or $NR_6R_7$ in which $R_6$ and $R_7$ are identical or different and are each linear or branched $C_1$–$C_{12}$alkyl, or in which $R_6$ and $R_7$, together with the nitrogen atom connecting them, form a 5-,6- or 7-membered ring which may include further heteroatoms, or by linear or branched $C_1$–$C_8$alkyl-$R_8$, in which $R_8$ is a radical $OR_5$, $COOR_5$ or $NR_6R_7$ with the above definitions or is $NH_2$, or by —N$^\oplus$$R_4R_6R_7$, in which $R_4$, $R_6$ and $R_7$ are as defined above, with the proviso that R and $R_1$ do not have the same definition if n and m are identical and $R_2$ and $R_3$ are both hydrogen and that, of the radicals $R_2$ and $R_3$, it is not the case that one is hydrogen and the other is phenyl.

The preferred definitions indicated above below the manganese complexes of formula (1) for n, m, Y, A, R, $R_1$, $R_2$ and $R_3$ are also preferred for the compounds of formula (1a).

The compounds of the formula (1) and (1a) are prepared, for example, in a conventional manner from the corresponding ligands and a manganese compound. Preparation processes of this kind are described, for example, in the U.S. Pat. Nos. 5,281,578 and 4,066,459. All of the manganese complexes mentioned therein, however, have symmetrically substituted ligands. Surprisingly, the manganese complexes of the invention, having asymmetric ligands, feature an enhanced specific action as catalysts for oxidations with peroxides.

The ligands of the formula

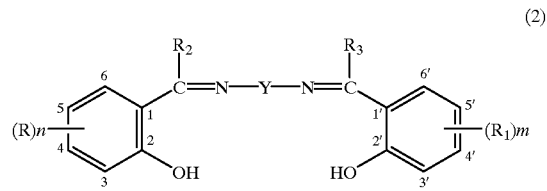

(2)

in which R, $R_1$, $R_2$, $R_3$, Y, n and m are as defined under the formula (1a) are likewise novel. They are prepared in a conventional manner by, for example, reacting a diamine of the formula $H_2N—Y—NH_2$ first with an aldehyde or ketone of the formula

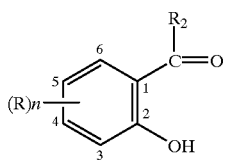

(3)

and then with an aldehyde or ketone of the formula

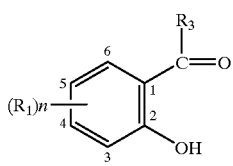

(4)

In the formulae (3) and (4) R, $R_1$, $R_2$, $R_3$, n and m are as defined under the formula (1), with the proviso that R and $R_1$ do not have the same definition if n and m are identical.

Of particular interest for use in the process of the invention are the compounds of the formula

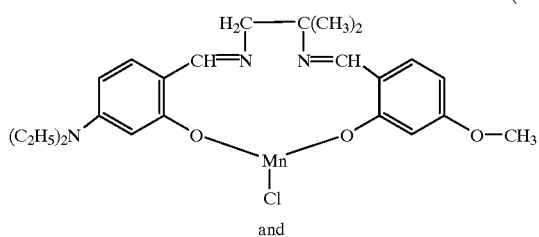

(1A)

and

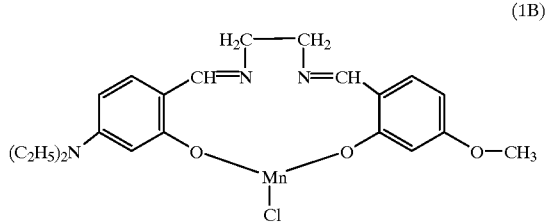

(1B)

It is also possible to employ the compounds of the formula (1) together with corresponding analogous symmetrical manganese complexes, i.e. with compounds of the formula (1) in which $(R)_n$ and $(R_1)_m$ are identical. Such mixtures are obtained, for example, by reacting a diamine of the formula $H_2N—Y—NH_2$ with a mixture of two different compounds of the formula (3) in the above synthesis of the ligands of the formula (2) and converting the resultant mixture comprising one asymmetric and two symmetrical ligands of the formula (2) into the corresponding Mn complexes.

The present invention additionally provides a detergent comprising

I) 5–90%, preferably 5–70% A) of an anionic surfactant and/or B) of a nonionic surfactant, II) 5–70%, preferably 5–50% and, in particular, 5–40% C) of a builder substance, III) 0.1–30%, preferably 1–12% D) of a peroxide, and IV) 0.005–2%, preferably 0.02–1% and, in particular, 0.1–0.5% E) of a compound of the above-defined formula (1), where the percentages are in each case by weight based on the overall weight of the detergent.

The detergent can be in solid or liquid form as, for example, a nonaqueous liquid detergent comprising not more than 5 and preferably from 0 to 1% by weight of water and as its base may have a suspension of a builder substance in a nonionic surfactant, as described, for example, in GB-A-2,158,454.

Preferably, however, the detergent is in powder or granule form.

This detergent can be prepared, for example, by first preparing an initial powder by spray-drying an aqueous slurry comprising all of the above-mentioned components with the exception of D) and E) and then adding the dry components D) and E) and mixing all of the components with one another.

Alternatively, component E) can be added to an aqueous slurry comprising components A), B) and C) which is then spray-dried, after which component D) can be mixed with the dry mass.

Yet another option is to start from an aqueous slurry which comprises components A) and C) but not, or not all of, component B). The slurry is spray-dried, then component E) is mixed with component B) and added, and, subsequently, component D) is admixed in dry form.

The anionic surfactant A) can be, for example, a sulfate, sulfonate or carboxylate surfactant or a mixture thereof.

Preferred sulfates are those with 12–22 carbon atoms in the alkyl radical, alone or in combination with alkyl ethoxysulfates whose alkyl radical has 10–20 carbon atoms.

Preferred sulfonates are, for example, alkylbenzenesulfonates with 9–15 carbon atoms in the alkyl radical.

The cation in the anionic surfactants is preferably an alkali metal cation, especially sodium.

Preferred carboxylates are alkali metal sarcosinates of the formula $R—CO—N(R^1)—CH_2COOM^1$, in which R is alkyl or alkenyl with 8–18 carbon atoms in the alkyl or alkenyl radical, $R^1$ is $C_1$–$C_4$alkyl and $M^1$ is an alkali metal.

The nonionic surfactant B) can be, for example, a condensation product of 3–8 mol of ethylene oxide with 1 mol of primary alcohol having 9–15 carbon atoms.

Examples of suitable builder substances C) are alkali metal phosphates, especially tripolyphosphates, carbonates or bicarbonates, especially their sodium salts, silicates, aluminium silicates, polycarboxylates, polycarboxylic acids, organic phosphonates, aminoalkylenepoly (alkylenephosphonates), or mixtures of these compounds.

Particularly suitable silicates are sodium salts of crystalline phyllosilicates of the formula $NaHSi_tO_{2t+1} \cdot pH_2O$ or $Na_2Si_tO_{2t+1} \cdot pH_2O$, in which t is a number between 1.9 and 4 and p is a number between 0 and 20.

Of the aluminium silicates, preference is given to those obtainable commercially under the names zeolite A, B, X and HS and to mixtures comprising two or more of these components.

Among the polycarboxylates, preference is given to the polyhydroxycarboxylates, especially citrates, and acrylates and also their copolymers with maleic anhydride.

Preferred polycarboxylic acids are nitrilotriacetic acid, ethylenediaminetetraacetic acid, and ethylenediaminedisuccinate, both in racemic form and in the enantiomerically pure S,S form.

Particularly suitable phosphonates or aminoalkylenepoly (alkylenephosphonates) are alkali metal salts of 1-hydroxyethane-1,1-diphosphonic acid, nitrilotris (methylenephosphonic acid), ethylenediaminetetramethylenepihosphonic acid and diethylenetriaminepentamethylenephosphonic acid.

Suitable peroxide components D) are, for example, the literature-referenced and commercially available organic and inorganic peroxides which bleach textile materials at customary washing temperatures: for example, at from 10 to 95° C.

The organic peroxides are, for example, mono- or polyperoxides, especially organic peracids or their salts, such as phthalimidoperoxycaproic acid, peroxybenzoic acid, diperoxydodecanedioic acid, diperoxynonanedioic acid, diperoxydecanedioc acid, diperoxyphthalic acid, or salts thereof.

It is preferred, however, to use inorganic peroxides, examples being persulfates, perborates, percarbonates and persilicates. It is of course also possible to use mixtures of inorganic and/or organic peroxides. The peroxides can be present in different crystal forms and with varying water content and may also be employed together with other organic or inorganic compounds in order to enhance their stability on storage.

Addition of the peroxides to the detergent takes place preferably by mixing the components with the aid, for example, of a screw metering system and/or a fluidized-bed mixer.

In addition to the combination of the invention the detergents may comprise one or more fluorescent whitening agents from the classes, for example, of bistriazinylaminostilbene-disulfonic acid, bistriazolylstilbenedisulfonic acid, bisstyrylbiphenyl or bisbenzofurylbiphenyl, or a bisbenzoxallyl derivative, bisbenzimidazolyl derivative, coumarin derivative or pyrazoline derivative.

In addition, the detergents may comprise soil antiredeposition agents, such as sodium carboxymethylcellulose, pH regulators, such as alkali metal or alkaline earth metal silicates, foam regulators, such as soap, salts for regulating spray drying and granulating properties, such as sodium sulfate, fragrances and, if desired, antistats and fabric softeners, enzymes, such as amylase, bleaches, pigments and/or shading agents. These constituents must of course be stable to the bleach that is employed.

Further preferred additions to the detergents of the invention are polymers which prevent stains due, when washing textiles, to dyes in the wash liquor that have become detached from the textiles under washing conditions. These are preferably polyvinylpyrrolidones, unmodified or modified by incorporation of anionic or cationic substituents, and especially those having a molecular weight in the range from 5000 to 60,000, in particular from 10,000 to 50,000. These polymers are employed preferably in an amount from 0.05 to 5% by weight, in particular from 0.2 to 1.7% by weight, based on the overall weight of the detergent.

In addition, the detergents of the invention may also include what are known as perborate activators, such as TAED or TAGU, for example. Preference is given to TAED, which is employed preferably in an amount from 0.05 to 5% by weight, in particular from 0.2 to 1.7% by weight, based on the overall weight of the detergent.

The examples which follow serve to illustrate the invention without restricting it to them. Parts and percentages are by weight unless specified otherwise.

EXAMPLE 1

N-Mono[4-(diethylamino)salicylidene]-2-methylpropane-1,2-diamine

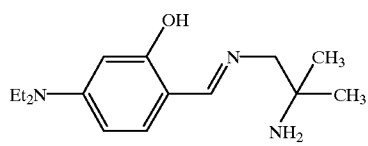

A solution of 4.56 g (0.0517 mol) of 1,2-diamino-2-methylpropane in 50 ml of ethanol is introduced as initial charge. At room temperature a solution of 10.0 g (0.0517 mol) of 4-N-diethylaminosalicylaldehyde in 50 ml of ethanol is added dropwise over the course of 2 h with stirring. After stirring for 2 h (TLC monitoring, acetonitrile/water 9:1) the reaction is complete. The reaction solution is carefully concentrated and the residue is dried under a high vacuum. The crude product obtained comprises 13.6 g of a dark red oil which is used subsequently without further purification.

EXAMPLE 2

N-Mono[4-(dimethylamino)salicylidene]-2-methylpropane-1,2-diamine

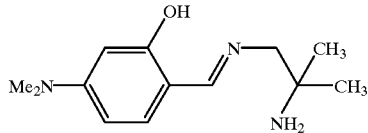

At room temperature a solution of 10.0 g (60.53 mmol) of 4-N-dimethylaminosalicylaldehyde in 100 ml of ethanol is added dropwise over the course of 2 h with stirring to 6.4 ml (5.3 g, 60.5 mmol) of 1,2diamino-2-methylpropane. After stirring for 2 h (TLC monitoring, acetonitrile/water 9:1) at room temperature the reaction is complete. The reaction solution is carefully concentrated and the residue is dried under a high vacuum. The crude product obtained comprises 14 g of a dark red oil which is reacted subsequently without further purification.

EXAMPLE 3

N-1-[4-(diethylamino)salicylidene]-N'-2-(4-methoxysalicylidene)-2-methylpropane-1,2-diamine (structure I) and N-2-[4-(diethylamino)salicylidene]-N'-1-(4-methoxysalicylidene)-2-methylpropane-1,2-diamine (structure II)

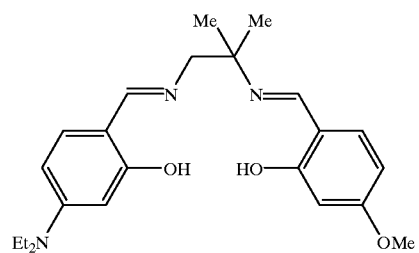

-continued

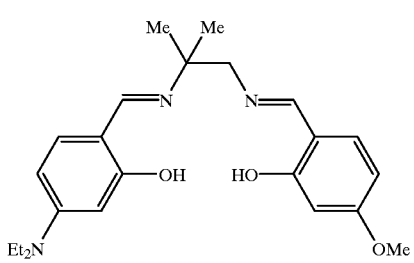

A suspension of 13.6 g (0.0517 mol) of N-Mono[4-(diethylamino)salicylidene]-2-methylpropane-1,2-diamine from Example 1 in 50 ml of ethanol is heated with stirring at 50° C. until a clear solution is obtained. 7.87 g (0.0517 mol) of 4-methoxysalicylaldehyde (solid) are added and the mixture is heated at reflux for 2 h. After that time the reaction is complete (TLC monitoring, ethyl acetate/methanol 9:1). Thereafter the reaction solution is carefully concentrated and the residue is dried under a high vacuum. The crude product obtained comprises 20 g of a dark red oil, which slowly solidifies. Purification is by column chromatography (eluent mixture: ethyl acetate/methanol 9:1). The asymmetrically substituted salen derivative is isolated as the diastereomer mixture (structures I and II). Yield: 7 g, reddish oil (34%). The product is characterized by $^1$H and $^{13}$C NMR spectroscopy.

$^{13}$C NMR (CDCl$_3$): δ=12.7 (CH$_3$CH$_2$N), 25.3, 25.4 ((CH$_3$)$_2$C—), 44.5 (NCH$_2$CH$_3$), 55.3 (OCH$_3$), 58.5, 59.3 (quat C, (CH$_3$)$_2$C—), 68.7, 69.3 (NCH$_2$), 98.0, 98.5, 101.2, 101.5, 103.0, 103.1, 106.2, 106.3, 133.0, 133.1 (tert aryl-C), 108.3, 108.4, 112.1, 112.3, 151.6, 151.9, 163.7, 163.9, 166.0, 166.7, 167.4, 168.4, (quat aryl-C), 159.2, 160.2, 164.8, 165.5 (C=N). MS (EI-MS) m/z: 397.3 (M)$^+$, 205, 192 (isomer I), 233 (isomer II)

EXAMPLE 4

N-1-[4-(Diethylamino)salicylidene]-N'-2-(4-hydroxysalicylidene)-2-methylpropane-1,2-diamine (structure I) and N-2-[4-(Diethylamino)salicylidene]-N'-1-(4-methoxysalicylidene)-2-methylpropane-1,2-diamine (structure II)

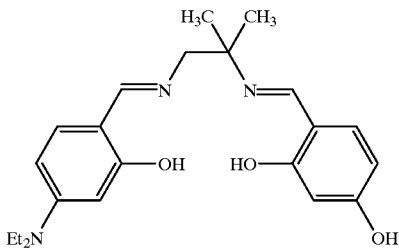

A solution of 1.36 g (5.17 mmol) of N-Mono[4-(diethylamino)salicylidene]-2-methylpropane-1,2-diamine from Example 1 in 5 ml of ethanol is admixed with 715 mg (5.17 mmol) of 4-hydroxysalicylaldehyde and the solution is heated at 60° C. for 3 h. After the end of the reaction (TLC monitoring, ethyl acetate/methanol 9:1) the reaction mixture is carefully concentrated and the residue is purified by column chromatography (250 g of silica gel, ethyl acetate/methanol 9:1). Yield: 244 mg (12%), isomer mixture.

$^{13}$C NMR (CD$_3$OD): δ=12.3 (CH$_3$CH$_2$N), 24.1, 24.5 (( CH$_3$)$_2$C—), 44.6 (NCH$_2$CH$_3$), 57.3, 58.6 (quat C), 63.0, 66.3 (=NCH$_2$), 98.9, 99.4, 100.1, 104.1, 104.3, 107.7, 134.6, 135.2, 135.8 (tert aryl-C), 108.2, 111.3, 111.6, 154.6, 155.1, 164.2, 165.0, 173.9, 175.9 (quat aryl-C), 158.3, 161.4, 163.5, 166.6 (C=N).

EXAMPLE 5

N-1-[4-(Diethylamino)salicylidene]-N'-2-(salicylidene)-2-methylpropane-1,2-diamine (structure I) and N-2-[4-(Diethylamino)salicylidene]-N'-1-(salicylidene)-2-methylpropane-1,2-diamine (structure II)

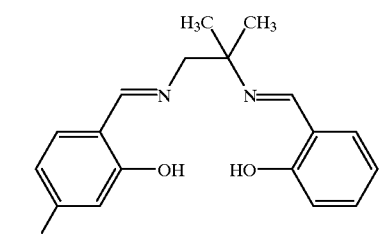

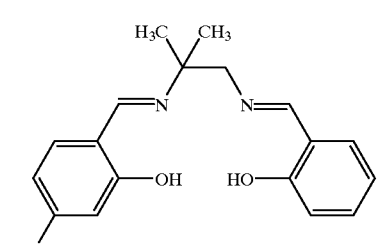

A solution of 13.62 g (0.0517 mol) of N-mono[4-(diethylamino)salicylidenel]-2-methylpropane-1,2-diamine from Example 1 in 50 ml of ethanol is heated to 50° C. and 5.5 ml (6.31 g, 0.0517 mol) of salicylaldehyde are added dropwise over the course of three minutes. During this addition the temperature of the solution rises by 5° C. The reaction solution is held at reflux for three hours, left to cool and concentrated on a rotary evaporator. This gives 19.31 g of a crude mixture which comprises the two diastereomers I and II. The crude mixture is resolved by column chromatography (ethyl acetate/methanol 9:1).

Yield: 4.01 g (21%) I, light brown solid, 1.55 g (8%) II, light brown oil.

NMR data I $^{13}$C NMR (CD$_3$OD): δ=12.2 (CH$_3$CH$_2$N), 23.9 (( CH$_3$)$_2$C), 44.5 (NCH$_2$CH$_3$), 60.1 (quat C(CH$_3$)$_2$), 62.0 (=N CH$_2$), 99.4, 104.3, 117.0, 118.6, 132.4, 132.8, 135.6 (tert aryl-C), 108.3, 119.1, 155.2, 162.2 (quat aryl-C), 162.8, 163.5 (C=N).

II $^{13}$C NMR (CD$_3$OD): δ=12.2 (CH$_3$CH$_2$N), 24.7 (( CH$_3$)$_2$C—), 44.5 (NCH$_2$CH$_3$), 57.1 (quat C(CH$_3$)$_2$), 69.3 (=NCH$_2$), 99.6, 104.1, 116.8, 118.9, 132.2, 132.8, 135.9 (tert aryl-C), 108.1, 119.1, 155.4, 161.4, 177.0 (quat aryl-C), 158.0, 168.4 (C=N).

EXAMPLE 6

N-[4-(Dimethylamino)salicylidene]-N'-(salicylidene)-1,2-ethylendiamine

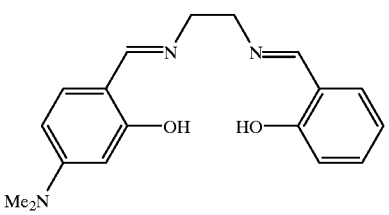

5.83 g (35.3 mmol) of 4-N-(dimethylamino)salicylaldehyde and 4.36 g (35.3 mmol) of salicylaldehyde are introduced into 30 ml of ethanol and the mixture is heated to 50° C. 2.27 ml (2.03 g, 33.6 mmol) of ethylenediamine are added over the course of 2 minutes.

During the addition the reaction temperature rises by about 15° C. The suspension is heated at 65° C. for 4 h. After cooling the reaction mass solidifies to give 14.2 g of a dark brown solid. 100 ml of a 9:1 ethyl acetate/methanol mixture are added to this solid and the resultant mixture is stirred for 2 h. The solid is filtered off and resuspended twice. The remaining solid is filtered off and the filtrate is concentrated. The residue is purified by column chromatography (450 g of silica gel, ethyl acetate/methanol 9:1). Yield: 1.3 g (12%).

$^{13}$C NMR (CD$_3$OD): δ=39.0 (N$\underline{C}$H$_3$), 53.3, 60.7 (=N$\underline{C}$H$_2$), 104.3, 117.0, 131.9, 132.1, 132.8, 132.9, 135.0, 135.2, 163.7, 167.3 (tert aryl-C), 118.5, 157.3, 161.6, 162.3 (quat aryl-C), 163.0, 168.0 ($\underline{C}$=N).

EXAMPLE 7
N-1-[4-(Dimethylamino)salicylidene]-N'-2-(salicylidene)-2-methylpropane-1,2-diamine (structure I) and N-2-[4-(dimethylamino)salicylidene]-N'-1-(salicylidene)-2-methylpropane-1,2-diamine (structure II)

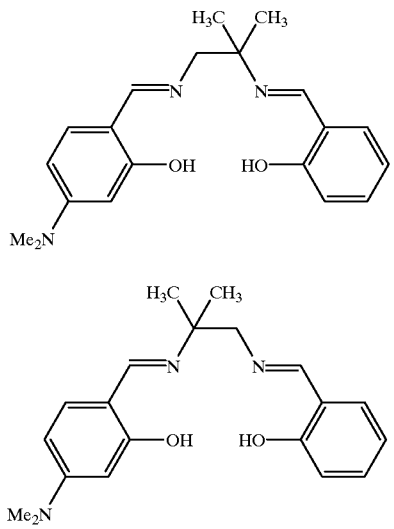

A solution of 7.67 g (30.3 mmol) of N-mono[4-(dimethylamino)salicylidene]-2-methylpropane-1,2-diamine from Example 2 in 50 ml of ethanol is heated to 50° C. At this temperature 3.70 g of salicylaldehyde (30.3 mmol) are added dropwise. The reaction solution is heated at reflux for 1 h. The dark brown suspension is concentrated. This gives 10.3 g of crude product which is purified by column chromatography (1 kg of silica gel, eluent: ethyl acetate/methanol 9:1). Yield: 1.7 g (16%) I yellowish solid, 0.81 g (8%) II, brownish solid.

Also isolated are 2.9 g (28%) of isomer mixture (composition according to $^1$H NMR 1.75 g of I, 1.17 g of II).

Isomer structure I:
$^1$H NMR (CDCl$_3$): δ=1.40 (s, 6H, CH$_3$), 3.00 (s, 6H, NCH$_3$), 3.60 (m, 2H, =NC$\underline{H}_2$), 6.12, 6.18, 6.83, 6.90, 6.98, 7.21, 7.25 (m, each 1H, tert aryl-H), 8.03, 8.32 (a, each 1H, C$\underline{H}$=N).
$^{13}$C NMR (CDCl$_3$): δ=25.0 (($\underline{C}$H$_3$)$_2$C—), 40.0 (NCH$_3$), 60.2 (quat $\underline{C}$(CH$_3$)$_2$), 68.9 (=NCH$_2$), 98.8, 103.5, 117.1, 131.4–132.1 (tert aryl-C), 108.8, 153.7 (quat aryl-C), 118.8 (tert aryl-C and quat aryl-C), 161.3 (C=N and quat aryl-C), 165.0 (C=N and quat aryl-C).

Isomer structure II:
$^{13}$C NMR (CDCl$_3$): δ=25.5 (($\underline{C}$H$_3$)$_2$C), 40.1 (NCH$_3$), 58.8 (quat C), 70.7 (NCH$_2$), 99.2, 103.4, 117.0, 118.6, 131.6, 132.3, 132.9 (tert aryl-C), 108.9, 154.0, 161.6 (quat aryl-C), 159.5, 166.5 ($\underline{C}$=N).

EXAMPLE 8
N-1-[4-(Dimethylamino)salicylidene]-N'-2-(4-hydroxysalicylidene)-2-methylpropane-1,2-diamine (structure I) and N-2-[4-(dimethylamino)salicylidene]-N'-1-(4-hydroxysalicylidene)-2- methylpropane-1,2-diamine (structure II)

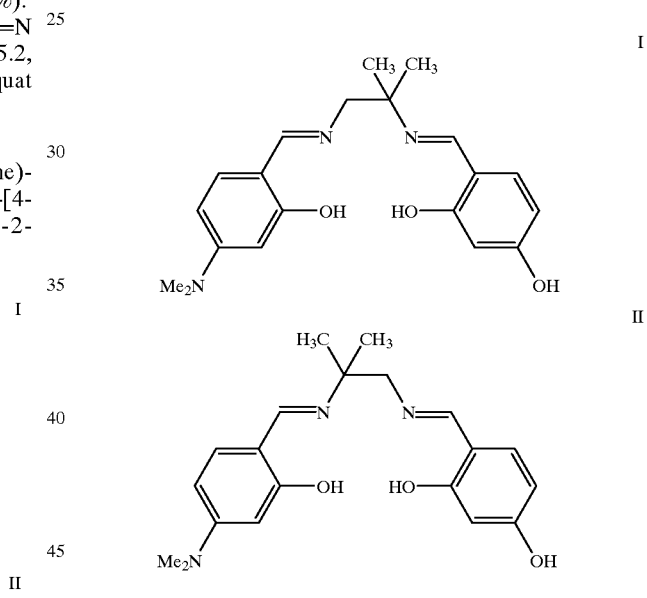

A solution of 7.67 g (30.3 mmol) of N-mono[4-(dimethylamino)salicylidene]-2-methylpropane-1,2-diamine from Example 2 in 50 ml of ethanol is heated to 55° C. At this temperature 4.18 g (30.3 mmol) of 2,4-dihydroxybenzaldehyde (solid) are introduced. The reaction mixture is subsequently heated at reflux until the starting material has disappeared (TLC monitoring, ethyl acetate/methanol 9:1). The greyish brown suspension is concentrated and the residue is dried under a high vacuum. This gives 10.8 g of crude product which is suspended in 50 ml of 9:1 ethyl acetate/methanol. The suspension is filtered, concentrated (1.38 g of crude product) and separated by column chromatography (ethyl acetate/methanol 9:1). Yield: 290 mg (3%), isomer mixture of I and II.

$^{13}$C NMR (DMSO-d$_6$): δ=26.0, 26.1 (($\underline{C}$H$_3$)$_2$C—), 40.3 (NCH$_3$), 59.2, 59.7 (quat C, $\underline{C}$(CH$_3$)$_2$), 68.6, 68.9 (NCH$_2$), 99.0, 99.2, 103.4, 103.6, 104.1, 104.3, 107.7, 133.6, 134.0, 134.3, 134.6 (tert aryl-C), 109.2, 109.4, 112.1, 154.4, 154.5, 162.7, 165.2, 165.5 (quat aryl-C), 161.3, 162.0, 166.3, 166.7 ($\underline{C}$=N).

EXAMPLE 9
N-1-[4-(Dimethylamino)salicylidene]-N'-2-(4-methoxysalicylidene)-2-methylpropane-1,2-diamine (structure I) und N-2-[4-(dimethylamino)salicylidene]-N'-1-(4-methoxysalicylidene)-2-methylpropane-1,2-diamine (structure II)

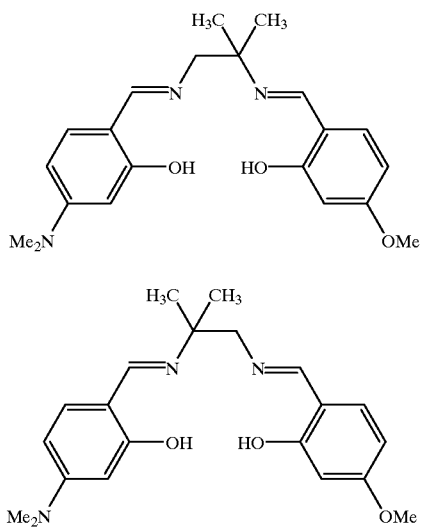

A solution of 7.67 g (30.27 mmol) of N-mono[4-(dimethylamino)salicylidene]-2-methylpropane-1,2-diamine from Example 2 in 50 ml of ethanol is heated to 50° C. At this temperature 4.6 g (30.27 mmol) of 4-methoxysalicylaldehyde are introduced. The mixture is heated at reflux for 2 h and cooled and the reaction solution is concentrated. The brown solid obtained (12.2 g) is purified by column chromatography (1 kg of silica gel, ethyl acetate/methanol 9:1). Yield: 4.69 g (42%), isomer mixture.

$^{13}$C NMR (CDCl$_3$): δ=25.3 ((CH$_3$)$_2$C), 40.3 (NCH$_3$), 55.3 (OCH$_3$), 58.6, 59.2 (quat C, C(CH$_3$)$_2$), 68.8, 69.2 (=NCH$_2$), 98.8, 99.2, 101.2, 101.4, 103.4, 103.5, 106.2, 106.4, 132.8, 133.1 (tert aryl-C), 108.7, 108.8, 112.1, 112.3, 153.8, 154.1, 163.7, 164.0, 166.8, 167.5 (quat aryl-C), 159.5, 160.2, 165.0, 165.5 (C=N).

EXAMPLE 10
N-[4-(Diethylamino)salicylidene]-N'-(4-methoxysalicylidene)-1,2-ethylendiamine

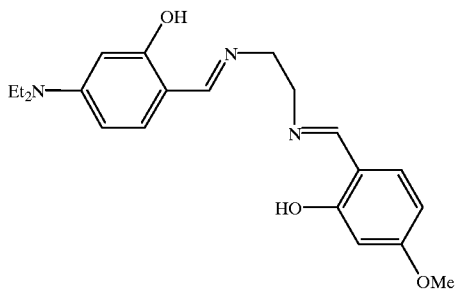

A solution of 3.87 g (0.0644 mol) of ethylenediamine in 300 ml of ethanol is introduced as initial charge and at room temperature a solution of 12.45 g (0.0644 mol) of 4-N-(diethylamino)salicylaldehyde in 60 ml of ethanol is slowly added dropwise with stirring. The solution is heated at reflux for 2 h. After it has cooled to room temperature, a solution of 9.8 g (0.0644 mol) of 4-methoxysalicylaldehyde in 25 ml of ethanol is slowly added dropwise. The reaction solution is subsequently heated at reflux temperature for 1 h. It is left to cool slowly and stirred at room temperature for 8 h. The resultant yellow suspension is worked up by concentration in vacuo and purified by column chromatography on silica gel (eluent: ethyl acetate/methanol 9:1). The asymmetric ligand is isolated as an orange oil.
Yield: 4.00 g (17%).
$^{13}$C NMR (CDCl$_3$): δ=12.7 (CH$_3$CH$_2$N), 44.4 (NCH$_2$CH$_3$), 55.3 (OCH$_3$), 58.1, 58.7 (NCH$_2$), 98.0, 101.2, 103.1, 106.3, 132.9, 133.0 (tert aryl-C), 108.3, 112.3, 151.5, 163.5 (quat aryl-C), 164.5, 165.4 (C=N).

EXAMPLE 11
N-[4-(Diethylamino)salicylidene]-N'-(4-hydroxysalicylidene)-1,2-ethylendiamine

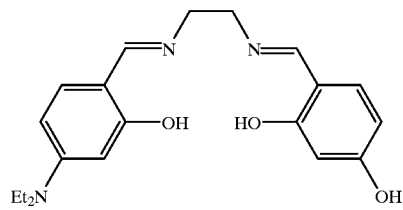

6.09 g (31.5 mmol) of 4-N-(diethylamino)salicylaldehyde and 4.35 g (31.5 mmol) of 2,4-dihydroxybenzaldehyde are introduced into 30 ml of ethanol and the mixture is heated to 50° C. 2 ml (1.80 g, 30 mmol) of ethylenediamine are added over the course of two minutes. During the addition the reaction temperature rises by about 10° C. The reaction solution is heated at 65° C. for 4 h. After cooling, the solution is concentrated to give 14.2 g of a dark brown oil. This oil is admixed with 100 ml of a 9:1 ethyl acetate/methanol mixture and the resultant mixture is stirred for 2 h. The suspension is filtered and concentrated. The residue is purified by column chromatography (450 g of silica gel, ethyl acetate/methanol 9:1).
Yield: 1.18 g (11%), orange oil.
$^{13}$C NMR (DMSO-d$_6$): δ=13.4 (CH$_3$CH$_2$N), 44.6 (NCH$_2$CH$_3$), 57.9, 58.6 (=NCH$_2$), 98.2, 103.5, 103.7, 107.8, 134.0, 134.3 (tert aryl-C), 108.6, 112.0, 126.3, 152.0, 162.8, 166.2 (quat aryl-C), 165.7, 166.6 (C=N).

EXAMPLE 12
N-[4-(Diethylamino)salicylidene]-N'-(salicylidene)-1,2-ethylendiamine

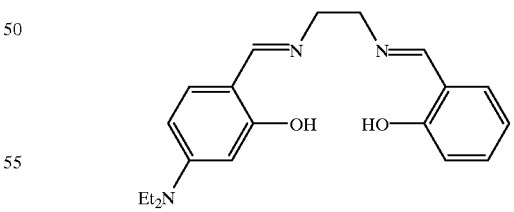

10 g (51.7 mmol) of 4-N-diethylaminosalicylaldehyde and 6.31 g (51.7 mmol) of salicylaldehyde are dissolved in 50 ml of ethanol. 3.1 g (51.7 mmol) of ethylenediamine are added at room temperature. During this addition the solution warms to about 40° C. It is heated at 70° C. for 3 h and left to cool. The reaction solution is concentrated to leave 21.6 g of a reddish brown oil. The crude product is purified by column chromatography (1 kg silica gel, ethyl acetate/methanol 20:1).

Yield: 1.5 g (8.5%).

$^{13}$C NMR (CD$_3$OD): δ=13.5 (CH$_3$CH$_2$N), 46.0 (NCH$_2$CH$_3$), 53.3, 60.7 (=NCH$_2$), 100.5, 105.7, 118.5, 120,3, 132.8, 133.5, 137.0 (tert aryl-C), 109.6, 156.6, 164.5, 177.2 (quat aromatics), 163.0, 169.5 (C=N).

EXAMPLE 13
(R,R)-N-[4-(Diethylamino)salicylidene]-N'-(salicylidene)-1,2-cyclohexanediamine

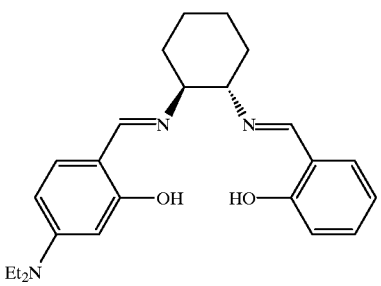

0.2 g (0.916 mmol) of (R,R)-N-mono(salicylidene)-1,2-cyclohexanediamine prepared in accordance with *Tetrahedron Letters* 39 (1998) 4199-4202 is dissolved in 20 ml of ethanol to give a clear yellow solution. At room temperature 177 mg (0.916 mmol) of 4-N-(diethylamino)salicylaldehyde dissolved in 20 ml of ethanol is added dropwise. The dark red reaction solution is heated at 60° C. for 4 h, then left to cool to room temperature and carefully concentrated on a rotary evaporator. This gives 386 mg of a red solid. This crude product is purified by column chromatography (30 g of silica gel, eluent: ethyl acetate).

Yield: 124.0 mg (34%) of honey-coloured honeycomb-like crystals.

$^{13}$C NMR (CDCl$_3$): δ=12.7 (CH$_3$CH$_2$N), 24.2, 24.4, 33.2, (cycl. CH$_2$), 44.4 (CH$_3$CH$_2$N), 70.9, 72.9 (tert cycl. CH), 97.9, 103.0, 116.7, 118.5, 131.5, 132.0, 132.9 (tert aryl-C), 108.2, 118.8, 151.3, 164.6, 165.3 (quat aryl-C), 161.1, 162.8 (C=N).

EXAMPLE 14
(R,R)-N-[4-(Dimethylamino)salicylidene]-N'-(salicylidene)-1,2-cyclohexanediamine

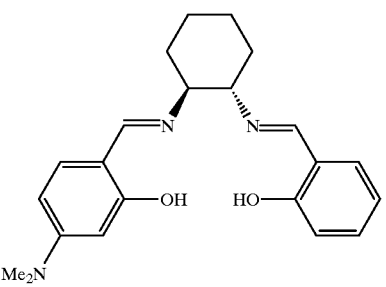

0.5 g (2.29 mmol) of (R,R)-N-mono(salicylidene)-1,2-cyclohexanediamine is reacted with 0.378 g (2.29 mmol) of 4-N-(dimethylamino)salicylaldehyde as described in the preceding example. Analogous workup gives a yellow solid as crude product (829 mg) which is purified by separation on a chromatography column (silica gel, ethyl acetate/methanol 9:1).

Yield: 318 mg (38%), pale yellow solid.

$^{13}$C NMR (CDCl$^3$): δ=24.2, 24.4, 33.2, (cycl. CH$_2$), 40.0 (N—CH$_3$), 71.1, 72.9 (tert cycl. CH), 98.7, 103.4, 116.7, 118.5, 131.5, 132.0, 132.6 (tert aryl-C), 108.7, 118.7, 153.6, 161.1 (quat aryl-C), 163.2, 164.7 (C=N).

EXAMPLE 15
(R,R)-N-[2-hydroxyacetophenone]-N'-(salicylaldehyde)-1,2-cyclohexanediimine

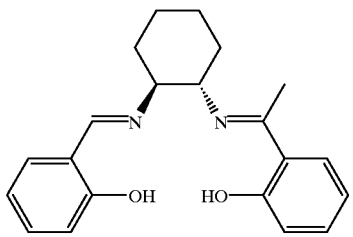

To a solution of 0.5 g (2.29 mmol) of (R,R)-N-mono(salicylidene)-1,2-cyclohexanediamine in 50 ml of ethanol is added dropwise 0.32 g (2.29 mmol) of 2-hydroxyacetophenone dissolved in 50 ml of ethanol. The mixture is heated at reflux temperature for 8 hours. Cooling and concentration of the reaction solution gives 714 mg of a brown solid. This crude product is purified by column chromatography (eluent: toluene/ethyl acetate 3:1).

Yield: 215.6 mg (28%), yellowish syrup.

$^{13}$C NMR (CDCl$_3$): δ=14.7 (CH$_3$), 24.2, 24.3, 32.3, 33.1 (cycl. CH$_2$), 62.3, 73.7 (tert cycl. CH), 116.8, 117.1, 118.6, 118.7, 128.3, 131.6, 132.3, 132.4 (tert aryl-C), 119.2, 160.9, 163.9, 170.8 (quat aryl-C), 164.8 (C=N).

EXAMPLE 16
(R,R)-N-mono[4-(diethylamino)salicylidene]-1,2-cyclohexanediamine

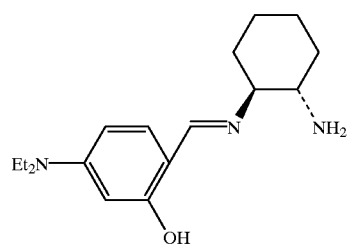

A solution of 3.95 g (34.55 mmol) of trans-1,2-diaminohexane in 770 ml of chloroform is admixed with 50 g of molecular sieve (4 Å) and cooled to −3° C. At this temperature 6.68 g (34.55 mmol) of 4-N-(diethylamino) salicylaldehyde dissolved in 250 ml of chloroform are added dropwise over the course of 5 h. Following the addition the reaction solution is allowed to warm to room temperature and is stirred for 8 h. The course of the reaction is monitored by TLC (mobile phase: ethyl acetate/methanol 9:1). After the end of the reaction the reaction solution is filtered and concentrated to give 9.9 g (100%) of crude product which is used subsequently without further purification.

Example 17
(R,R)-N-[4-(Diethylamino)salicylidene]-N'-(4-hydroxysalicylidene)-1,2-cyclohexanediamine

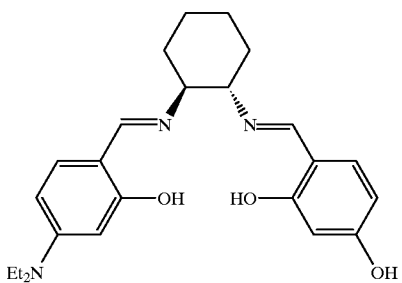

To a suspension of 2.5 g (8.64 mmol) of (R,R)-N-mono[4-(diethylamino)salicylidene]-1,2-cyclohexanediamine in 200 ml of ethanol is added dropwise at room temperature over the course of 45 minutes a solution of 1.19 g (8.64 mmol) of 2,4-dihydroxybenzaldehyde. The suspension is heated at 60° C. for 4 h. After cooling to room temperature the resultant brownish orange solution is concentrated to dryness. The crude product (3.5 g) is resolved by column chromatography (ethyl acetate/methanol 9:1). Yield: 570 mg (16%), yellowish orange solid.

$^{13}$C NMR (CDCl$_3$): δ=12.4($\underline{C}$H$_3$CH$_2$N), 23.8, 32.7, 32.8 (cycl.-CH$_2$), 43.7 (CH$_3$$\underline{C}$H$_2$), 70.2, 70.6 (tert cycl. CH), 97.1, 102.3, 102.7, 106.7, 132.8, 133.1 (tert aryl-C), 107.6, 111.1, 150.7, 161.4, 163.9 (quat aryl-C), 163.1, 163.8 ($\underline{C}$=N).

EXAMPLE 18
(R,R)-N-[4-(Diethylamino)salicylidene]-N'-(4-methoxysalicylidene)-1,2-cyclohexanediamine

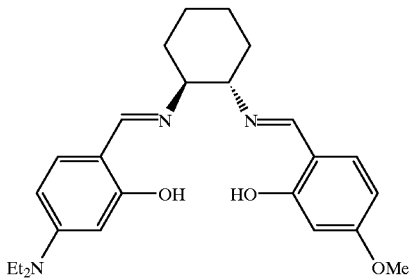

To a suspension of 2.5 g (8.64 mmol) of (R,R)-N-mono[4-(diethylamino)salicylidene]-1,2-cyclohexanediamine in 200 ml of ethanol is added dropwise over the course of 45 minutes at room temperature a solution of 1.3 g (8.64 mmol) of 4-methoxysalicylaldehyde in 200 ml of ethanol. The reaction solution is heated at 60° C. for 4 h. After the reaction solution has been cooled to room temperature it is concentrated to dryness. The crude product obtained is purified by column chromatography (ethyl acetate/methanol 9:1). Yield: 500 mg (14%), reddish orange oil, which slowly crystallizes.

$^{13}$C NMR (CDCl$_3$): δ=12.7 ($\underline{C}$H$_3$CH$_2$N), 24.3, 33.2 (cycl.-CH$_2$), 44.4 (CH$_3$$\underline{C}$H$_2$N), 55.3 (OCH$_3$), 70.9, 71.5, 71.6 (tert cycl. CH), 98.0, 101.1, 103.0, 106.1, 106.2, 132.9 (tert aryl-C), 108.2, 112.3, 151.3, 165.5 (quat aryl-C), 162.9, 163.7 ($\underline{C}$=N).

Synthesis of the Manganese Complexes:

EXAMPLE 19
[N-[4-(Diethylamino)salicylidene]-N'-(4-methoxysalicylidene)-1,2-ethylendiaminato]mangan(III)-chlorid

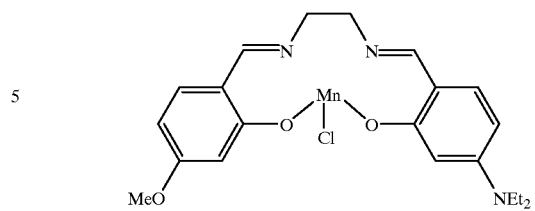

Procedure: 200 mg (0.541 mmol) of ligand from Example 10 are dissolved in 11 ml of ethanol. 133 mg (0.541 mmol) of manganese(II) acetate tetrahydrate are introduced into this clear orange solution. There is a colour change to dark red, and a precipitate is formed. The mixture is heated at 70° C. for 4 h, during which the precipitate goes into solution. The reaction solution is subsequently concentrated to dryness on a rotary evaporator. This gives 306 mg of a solid which is dissolved in 11 ml of distilled water. The product is precipitated with 0.54 g of sodium chloride. It is purified by stirring for 10 minutes, filtered off and dried in vacuo at 50° C.

Yield: 220 mg (89%), reddish black solid.

EXAMPLE 20
[N-2-[4-(Diethylamino)salicylidene]-N'-1-(salicylidene)-2-methylpropane-1,2-diaminato]mangan(III)-chlorid

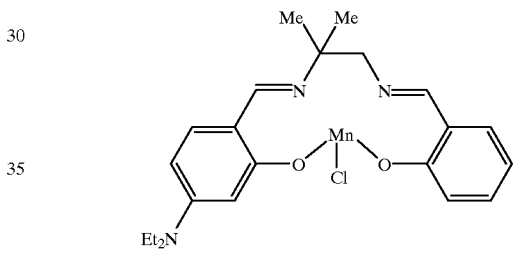

1.2 g (3.25 mmol) of ligand II from Example 5 are dissolved in 65 ml of ethanol. At room temperature 0.80 g (3.25 mmol) of manganese(II) acetate tetrahydrate is added to this yellowish orange solution. There is a colour change to red. The reaction mixture is heated at 65–70° C. for 4 h. The reaction mixture is concentrated to dryness, the residue is taken up with 65 ml of distilled water, and the complex is precipitated with 3.25 g of sodium chloride, isolated by filtration and dried to constant mass under a high vacuum at 50° C. Yield: 1.1 g (74%), reddish brown solid.

EXAMPLE 21
[N-1-[4-(Dimethylamino)salicylidene]-N'-2-(salicylidene)-2-methylpropane-1,2-diaminato]mangan(III)-chlorid

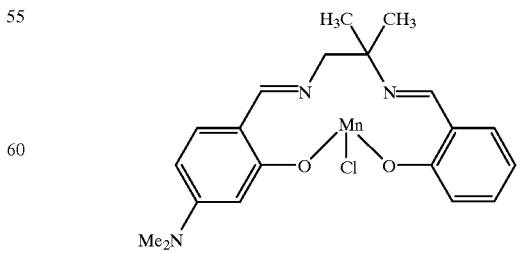

A suspension of 1 g (2.95 mmol) of ligand I from Example 7 in 60 ml of ethanol is admixed with 0.72 g (2.95 mmol) of manganese(II) acetate tetrahydrate. The reaction machine and work-up (precipitation with 6 g of sodium chloride) are analogous to those of Example 20.

Yield: 924 mg (73%), reddish brown solid.

EXAMPLE 22

[N-2-[4-(Dimethylamino)salicylidene]-N'-1-(salicylidene)-2-methylpropane-1,2-diaminato]mangan(III)-chlorid

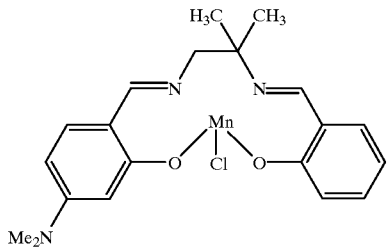

A solution of 529 mg (1.56 mmol) of ligand II from Example 7 in 30 ml of ethanol is reacted with 380 mg (1.56 mmol) of manganese(II) acetate tetrahydrate and the product is precipitated with 3.1 g of sodium chloride as described in Example 20. Yield: 929 mg. The metal complex still contains sodium chloride and was used without further purification.

EXAMPLE 23

[N-[4-(Diethylamino)salicylidene]-N'-(4-hydroxysalicylidene)-1,2-ethylendiaminato]mangan(III) chlorid

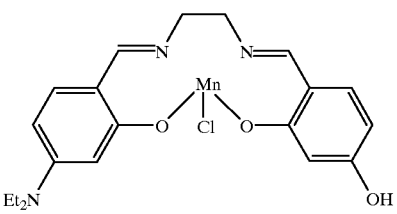

300 mg (0.844 mmol) of ligand from Example 11 are suspended in 17 ml of ethanol, and 207 mg (0.844 mmol) of manganese(II) acetate tetrahydrate are added to the suspension. There is a colour change to red. The reaction mixture is heated to reflux over the course of 30 minutes and then held at 65–70° C. for 3 h. The solution is concentrated to give 419 mg of a solid which is taken up in 17 ml of distilled water. The complex is precipitated by introducing 0.84 g of sodium chloride, isolated by filtration and dried.

Yield: 314 mg (84%), dark red solid.

EXAMPLE 24

[N-1-[4-(Diethylamino)salicylidene]-N'-(4-methoxysalicylidene)-2-methylpropane-1,2-diaminato]mangan(III)-chlorid (structure I) and [N-2-[4-(Diethylamino)salicylidene]-N'-1-(4-methoxysalicylidene)-2-methylpropane-1,2-diaminato]mangan(III)chlorid (structure II)

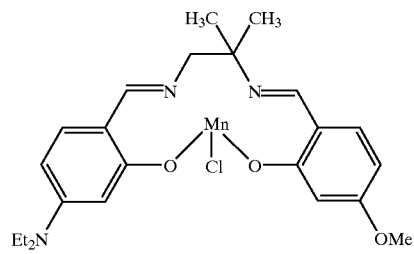

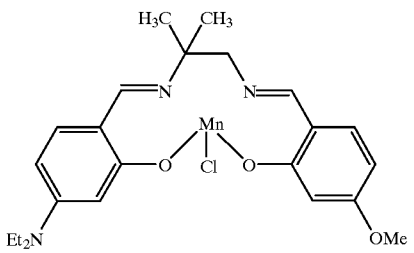

3 g (7.5 mmol) of ligand (mixture of isomeres) from Example 3 are dissolved in 150 ml of ethanol. To this light brown solution, which is yellow at high levels of dilution, are added 1.85 g (7.5 mmol) of manganese(II) acetate tetrahydrate. There is an immediate colour change to red. The clear solution is heated at 65–70° C. for 4 h and, after cooling, is concentrated. The dark red oil obtained (4.33 g) is taken up in 150 ml of distilled water. The complex is precipitated with 7.5 g of sodium chloride, isolated by filtration and dried.

Yield: 2.68 g (73%), dark red solid, mixture of isomeres.

EXAMPLE 25

[N-[4-(Diethylamino)salicylidene]-N'-(salicylidene)-1,2-ethylendiaminato]mangan(III)chlorid

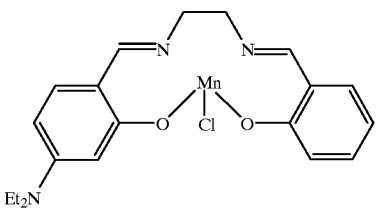

A solution of 194 mg (0.57 mmol) of ligand from Example 12 in 10 ml of ethanol is admixed with 140 mg (0.57 mmol) of manganese(II) acetate tetrahydrate. There is a colour change from reddish brown to blood-red. The reaction solution is boiled under reflux for 3 h, left overnight with stirring and heated for a further 3 h. After cooling, it is concentrated to dryness and the residue is taken up with 10 ml of distilled water, precipitated with 1.5 g of sodium chloride, isolated by filtration and dried under a high vacuum. The product still contains sodium chloride and is used without further purification.

EXAMPLE 26

[N-i-[4-(Diethylamino)salicylidene]-N'-2-(salicylidene)-2-methylpropane-1,2-diaminato]mangan(III)chlorid

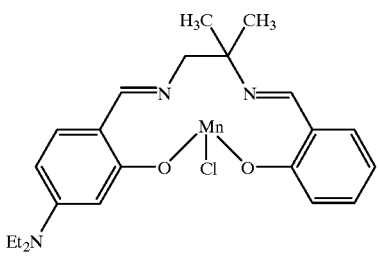

1.0 g (4.08 mmol) of manganese(II) acetate tetrahydrate is introduced into a solution of 1.5 g (4.08 mmol) of ligand I from Example 5 in 80 ml of ethanol. The resultant solution isheated at 65° C. for 2 hours. After cooling it is concentrated to dryness and the residue is taken up in 80 ml of distilled water, after which the product is precipitated with 4.1 g of sodium chloride, isolated by filtration and dried under a high vacuum. Yield: 1.51 g (81%).

EXAMPLE 27
[N-[4-(Dimethylamino)salicylidene]-N'-(salicylidene)-1,2-ethylendiaminato]mangan(III)chlorid

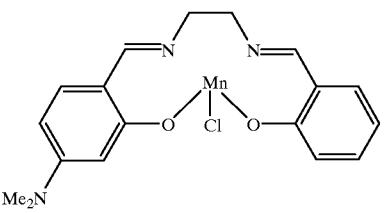

86.5 mg (0.353 mmol) of manganese(II) acetate tetrahydrate are introduced into a solution of 110 mg (0.353 mmol) of the ligand from Example 6 in 5 ml of ethanol. The reddish brown solution obtained is heated at 65° C. for 2 hours. After cooling, the solution is concentrated to dryness, the residue is taken up in 5 ml of distilled water, and the product is precipitated with 200 mg of sodium chloride, isolated by filtration and dried under a high vacuum. Yield: 61 mg (43%).

EXAMPLE 28
(R,R)-N-[4-(dimethylamino)salicylidene]-N'-(4-hydroxysalicylidene)-1,2-cyclohexanediamine

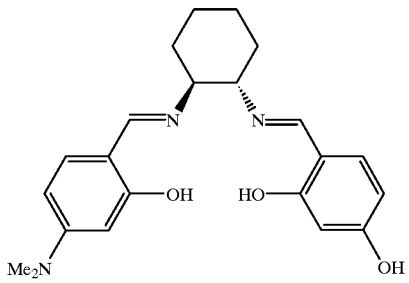

To a solution of 2.5 g (9.56 mmol) (R,R)-N-mono(4-dimethylamino)salicylidene)-1,2-cyclohexanediamine in 225 ml of ethanol is added dropwise at room temperature over the course of 45 minutes a solution of 1.321 g (9.56 mmol) 2,4-dihydroxybenzaldehyde in 225 ml ethanol. The reaction solution is heated at 60° C. for 4 h. After cooling to room temperature the resultant reddish brown solution is concentrated to dryness. The crude product (ca. 5 g) is resolved by column chromatography (ethyl acetate/methanol 9:1). Yield: 1,09 g (30%), yellowish orange solid.

$^{13}$C NMR (DMSO—$d_6$): δ=23.7, 32.7, 32.8 (cycl. $CH_2$), 40.0 ($NCH_3$), 70.3, 70.7 (tert. cycl. CH), 97.9, 102.3, 103.2, 106.7, 132.5, 133.1 (tert. aryl-C), 108.1, 111.1, 153.1, 161.4 (quart. aryl-C), 163.4, 163.9 ($\underline{C}$=N).

EXAMPLE 29
(R,R)-N-[4-(dimethylamino)salicylaldehyde]-N'-(2-hydroxyacetophenone)-1,2-cyclohexanediimine

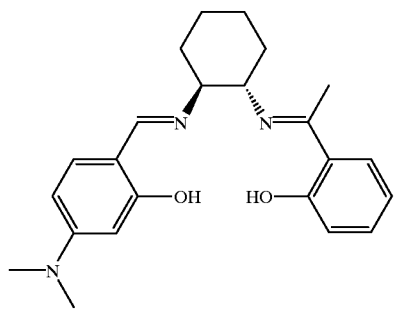

To a solution of 2.5 g (9.56 mmol) (R,R)-N-mono(4-dimethylaminosalicylidene)-1,2-cyclohexanediamine in 225 ml of ethanol is added dropwise a solution of 1.30 g (9.56 mmol) 2-hydroxyacetophenone in 225 ml ethanol. The reaction solution is heated at 60° C. for 8 h. The resulting reddish brown clear solution is stirred for further 4 hours at room temperature and concentrated to dryness in high vacuo. The crude product (3,6 g, dark red oil) is resolved by column chromatography (ethyl acetate/methanol 9:1). Yield: 1.60 g (44%), reddish orange foam.

$^{13}$C NMR ($CDCl_3$): δ=14.7 ($CH_3$), 24.2, 24.3, 32.4, 33.2 (cycl. $CH_2$), 40.0 ($NCH_3$), 62.3, 72.2 (tert. cycl. CH), 98.6, 103.4, 116.8, 118.6, 128.3, 132.3, 132.7 (tert. Aryl-C), 108.6, 119.1, 153.6, 164.3, 170.9 (quart. Aryl-C), 163.2 ($\underline{C}$=N).

$C_{23}H_{29}N_3O_2$ (379.5)

EXAMPLE 30
N-Mono[4-(diethylamino)salicylidene]-1,2-phenylenediamine

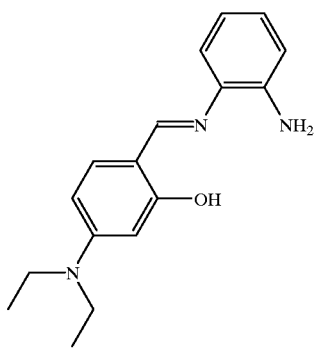

3.479 g (17.64 mmol) 4-(N,N-Diethylamino)-salicylaldehyde are added at 5° C. in portions to a solution of 1.927 g (17.64 mmol) 1,2-phenylenediamine in 18 ml ethanol, the temperature being kept below 10° C. The resultant dark red suspension is stirred for 8 hours at room temperature and concentrated to dryness in vacuo. The crude product (6.34 g) is resolved by column chromatography (n-hexane/ethyl acetate 65:35). Yield: 1.27 g (26%), golden yellow crystalls.

$^{13}$C NMR (CDCl$_3$): δ=12.7 (CH$_3$), 44.6 (CH2), 97.6, 103.7, 115.4, 118.2, 118.8, 126.6, 133.7 (tert. aryl-C), 109.3, 136.4, 140.4, 151.6, 163.2 (quart. aryl-C), 160.9 (C=N).

EXAMPLE 31

N-[4-(diethylamino)salicylidene]-N'-(salicylidene)-1,2-phenylenediamine

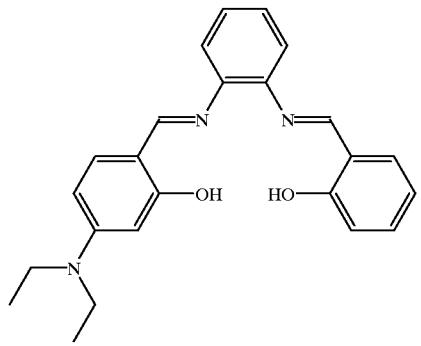

To a yellowish brown suspension of 0.3 g (1.06 mmol) N-Mono[4-(diethylamino)-salicylidene]-1,2-phenylenediamine from example 30 in 2 ml ethanol are added dropwise at 60° C. 129 mg (112 μl, 1.06 mmol) salicylaldehyde. The reaction slolution is stirred for 5 hours at 75° C. and after cooling to room temperature concentrated to dryness. The crude product is resolved by column chromatography (n-hexane/ethyl acetate 65:35). Yield: 139 mg (34%), colourless oil.

$^{13}$C NMR (CDCl$_3$): δ=11.7 (CH$_3$CH$_2$N), 44.4 (CH$_3$CH$_2$N), 97.0, 102.4 (tert. aryl-H), 116.5–119.0, 125.1, 126.6, 130.0–132.0 (tert. aryl-C), 108.3, 118.3, 141.1, 141.4, 151.2, 160.3 (quart. aryl-C), 159.5, 162.4 (C=N).

C$_{24}$H$_{25}$N$_3$O$_2$ (387.5)

EXAMPLE 32

Preparation of a mixture of asymmetric and symmetrical manganese(III)-salene complexes The asymmetric salene complexes described can also be used, without complicated purification, as a mixture of different metal complexes. 4.74 g of crude mixture from Example 5 are diluted with 250 ml of ethanol to give a clear brown solution. 3.17 g (12.9 mmol) of manganese(II) acetate tetrahydrate are added, accompanied by a colour change to red. The mixture is reacted at 65–70° C. for 4 hours and then concentrated to dryness. The resultant solid is taken up in 250 ml of distilled water, salted out with 26 g of sodium chloride and dried under a vacuum. The crude mixture is applied directly. The crude product comprises the asymmetric metal complexes from Examples 20 and 26 and also the metal complexes of the symmetrical ligand of structure:

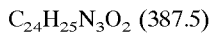

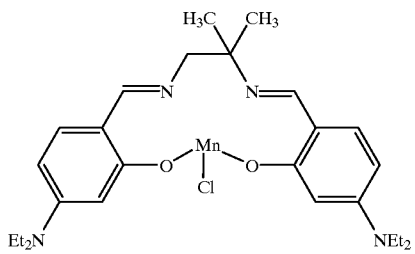

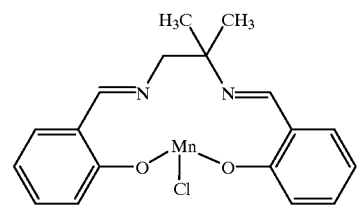

EXAMPLE 33

To investigate the effectiveness of the catalysts, the DTI efficacy is measured. The DTI (Dye transfer inhibition) efficacy a is defined as the following percentage:

$$a=([Y(E)-Y(A)]/[Y(W)-Y(A)]) * 100$$

where Y(W), Y(A) and Y(E) are the CIE lightnesses of the white material, of the material treated without added catalyst and of the material treated with added catalyst, in that order. a=0 characterizes a completely useless product whose addition to the washing liquor gives free rein to dye transfer. a=100%, on the other hand, corresponds to a perfect catalyst which completely suppresses the staining of the white material.

The test data are determined using the following test system: 7.5 g of white cotton fabric are treated in 80 ml of washing liquor. This liquor contains the standard detergent ECE phosphate-free (456 IEC) EMPA, Switzerland, in a concentration of 7.5 g/l, 8.6 mmol/l H$_2$O$_2$ and a solution of the test dye. The washing process takes place in a cup in a LINITEST apparatus at 40° C. for 30 minutes. In this test the catalysts are employed as per standard in the stated concentrations.

The following commercially obtainable dyes are employed as test dyes:

| Dye 1 | (F1) | Direct Brown 172 |
| Dye 4 | (F4) | Reactive Blue 238 |
| Dye 6 | (F6) | Reactive Black 5 |
| Dye 8 | (F8) | Direct Blue 71 |
| Dye 9 | (F9) | Direct Black 22 |
| Dye 10 | (F10) | Anionic Blue 113 |
| Dye 13 | F(13) | Disperse Violet 1 |
| Dye 14 | (F14) | Reactive Blue 19 |

The reflection spectra of the samples were measured with a SPECTRAFLASH 2000 and converted into lightnesses (D65/10) by a standard procedure in accordance with CIE.

The following table shows the results with the catalyst obtained according to Example 24 (Mn complex). It shows the DTI effects (a) as a function of catalyst concentration under service conditions as described above.

TABLE 1

| Catalyst concentration μmol/l | DTI effect (a) | |
| --- | --- | --- |
| | Dye 1 | Dye 2 |
| 5 | 62 | 76 |
| 20 | 85 | 90 |
| 30 | 89 | 90 |
| 50 | 91 | 91 |

The following table shows that the catalyst obtained in accordance with Example 24 very effectively prevents the redeposition of dyes of various classes. The values indicated here relate to a catalyst concentration of 50 μmol/l and experimental conditions as described above.

TABLE 2

| Test Dye | Dye concentration mg/l | DTI effect (a) |
| --- | --- | --- |
| Direct Brown 172 250% | 10 | 91 |
| Reactive Blue 238 100% | 6 | 91 |
| Reactive Black 5 133% | 12 | 95 |
| Direct Black 022 400% | 6 | 85 |
| Reactive Black 19 (Special) 100% | 20 | 100 |
| Anionic Blue 113 180% | 6 | 99 |
| Disperse Violet 1 100% | 6 | 86 |

The catalyst has the further feature that even at a service temperature of only 20° C. the great majority of the protective effect observed at 40° C. is retained.

TABLE 3

| Catalyst concentration μmol/l | DTI effect (a) | |
| --- | --- | --- |
| | Dye 1 | Dye 2 |
| 5 | 57 | 78 |
| 20 | 80 | 89 |
| 30 | 84 | 90 |
| 50 | 85 | 87 |

The catalyst features an acceptable balance of damage relative to coloured laundry. In terms of dye damage, even when using dyes known to be highly sensitive, the degradation is only of the same order of magnitude as observed with the TAED-activated bleaching system. In the sector of oxygen bleaches, the latter is considered prior art with an acceptable damage/benefit balance. When used as described above, the following percentage dye loss is found after fivefold treatment.

TABLE 4

| Test dye | Dye loss % | |
| --- | --- | --- |
| | Catalyst 50 μmol/l | TAED |
| Vat Brown 1 | 11 | 2 |
| Reactive Brown 17 | 16 | 15 |
| Reactive Red 123 | 14 | 13 |
| Direct Blue 85 | 22 | 14 |

In terms of fibre damage on dyed materials, the catalyst exhibits a better balance than the quoted TAED system. When used as described above, the following relative DP lowering is found after fivefold treatment.

TABLE 5

| Test dye | Relative DP lowering % | |
| --- | --- | --- |
| | Catalyst 50 μmol/l | TAED |
| Reactive Brown 017 | 2 | 5 |
| Vat Brown 001 | 9 | 19 |
| Reactive Red 123 | 4 | 7 |
| Direct Blue 085 | 10 | 15 |

EXAMPLE 34

Conducting DTI screening with the following isolated ligands, which were converted into the manganese complexes immediately before the screening by the an in situ process, gives the results shown in Table 6.

TABLE 6

| Mn-complexes of the ligands from Example No. | a (%) 10 μM (F1) | a (%) 20 μM (F1) | a (%) 10 μM (F4) | a (%) 20 μM (F4) |
| --- | --- | --- | --- | --- |
| 4 | 70 | 77 | 74 | 84 |
| 8 | 74 | 81 | 77 | 79 |
| 9 | 72 | 79 | 75 | 80 |
| 13 | | 76 | | 53 |
| 14 | 82 | 85 | 84 | 88 |
| 15 | | 73 | | |
| 17 | 86 | 86 | 87 | 86 |
| 18 | 85 | 88 | 80 | 90 |

Table 7 shows the results obtained when DTI screening is conducted with the isolated Mn complexes.

TABLE 7

| Manganese complexes from Example No. | a (%) 10 μM (F1) | a (%) 20 μM (F1) | a (%) 10 μM (F4) | a (%) 20 μM (F4) |
| --- | --- | --- | --- | --- |
| 19 | 78 | 87 | 85 | 93 |
| 20 | 86 | 91 | 94 | 87 |
| 21 | | 80 | | 62 |
| 22 | | 90 | | 96 |
| 23 | 62 | 89 | 82 | 95 |
| 24 | 81 | 88 | 95 | 94 |
| 25 | 80 | 89 | 90 | 95 |
| 26 | 77 | 81 | 83 | 86 |
| 27 | 78 | 77 | 54 | 72 |
| 28 | | | | |

EXAMPLE 35

The asymmetric salen complexes described exhibit an excellent action even at reduced peroxide concentration. If the concentration of peroxide is reduced from 8.6 mM to 0.17 mM, then the DTI effect is fully retained. Table 8 below shows the effect of the metal complex from Example 20 with a reduced amount of peroxide.

TABLE 8

| Dye | a [%] 0.17 mM $H_2O_2$ | a [%] 0 mM $H_2O_2$ | a [%] 8.6 mM $H_2O_2$ |
| --- | --- | --- | --- |
| F1 | 82 | 48 | 90 |
| F4 | 93 | 55 | 95 |

TABLE 8-continued

| Dye | a [%] 0.17 mM $H_2O_2$ | a [%] 0 mM $H_2O_2$ | a [%] 8.6 mM $H_2O_2$ |
|---|---|---|---|
| F6 | 93 | 54 | 95 |
| F8 | 79 | 1 | 75 |
| F9 | 83 | 48 | 85 |
| F10 | 90 | 71 | 95 |
| F13 | 89 | 65 | 85 |
| F14 | 93 | 31 | 95 |

What is claimed is:

1. A process which prevents the redeposition of migrating dyes in a wash liquor, which comprises adding to the wash liquor, which comprises a peroxide-containing detergent, from 0.5 to 150 mg per liter of wash liquor of at least one asymmetrical compound of the formula

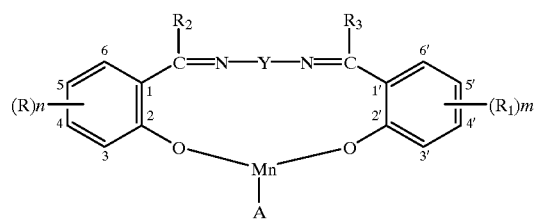

(1)

in which n is 0, 1, 2 or 3, m is 1, 2 or 3,

A is an anion;

Y is a linear or branched alkylene radical of the formula
—[C($R_5$)$_2$]$_r$—, where r is an integer from 1 to 8 and the $R_5$ radicals independently of one another are hydrogen or $C_1$–$C_4$alkyl;
—CX=CX—, in which X is cyano, linear or branched $C_1$–$C_8$alkyl or di(linear or branched $C_1$–$C_8$alkyl)-amino,
—(CH$_2$)$_q$—NR$_4$—(CH$_2$)$_q$—, in which $R_4$ is hydrogen or linear or branched $C_1$–$C_4$alkyl and q is 1, 2, 3 or 4;
or a 1,2-cyclohexylene radical of the formula:
—(CH$_2$)$_q$—NR$_4$—(CH$_2$)$_q$—, in which $R_4$ is hydrogen or linear or branched $C_1$–$C_4$alkyl and q is 1, 2, 3 or 4;
or a 1,2-cyclohexylene radical of the formula:

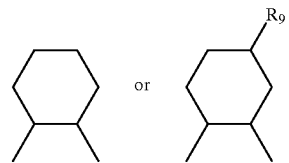

or a 1,2-aryl radical of the formula

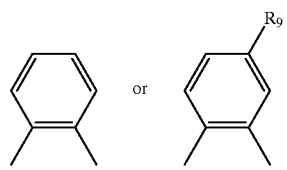

in which $R_9$ is $SO_3H$, $CH_2OH$ or $CH_2NH_2$,

R and $R_1$ independently of one another are cyano, halogen, OR$_5$ or COOR$_5$, in which $R_5$ is hydrogen or linear or branched $C_1$–$C_4$alkyl, or are nitro, linear or branched $C_1$–$C_8$alkyl, linear or branched, partially fluorinated or perfluorinated $C_1$–$C_8$alkyl, NHR$_6$ or NR$_6$R$_7$ in which $R_6$ and $R_7$ are identical or different and are each linear or branched $C_1$–$C_{12}$alkyl or in which $R_6$ and $R_7$, together with the nitrogen atom connecting them, form a 5-, 6- or 7-membered ring which may include further heteroatoms, or are linear or branched $C_1$–$C_8$alkyl-$R_8$, in which $R_8$ is a radical OR$_5$, COOR$_5$ or NR$_6$R$_7$ with the above definitions or is NH$_2$, or are —N$^\oplus$R$_4$R$_6$R$_7$, in which $R_4$, $R_6$ and $R_7$ are as defined above, $R_2$ and $R_3$ independently of one another are hydrogen, linear or branched $C_1$–$C_4$ alkyl or unsubstituted aryl, or aryl substituted by cyano, halogen, OR$_5$ or COOR$_5$, in which $R_5$ is hydrogen or linear or branched $C_1$–$C_4$alkyl, or by nitro, linear or branched $C_1$–$C_8$alkyl, NHR$_6$ or NR$_6$R$_7$ in which $R_6$ and $R_7$ are identical or different and are as defined above, or by linear or branched $C_1$–$C_8$alkyl-$R_8$, in which $R_8$ is a radical OR$_5$, COOR$_5$ or NR$_6$R$_7$ with the above definitions or is NH$_2$, or by —N$^\oplus$R$_4$R$_6$R$_7$, in which $R_4$, $R_6$ and $R_7$ are as defined above, with the proviso that R and $R_1$ do not have the same definition if n and m are identical.

2. A process according to claim 1, wherein from 1.5 to 75 mg per liter of washing liquor of one or more compounds of the formula (1) are added.

3. A process according to claim 2, wherein from 7.5 to 40 mg per liter of washing liquor of one or more compounds of the formula (1) are added.

4. A process according to claim 1, wherein the anion A is halide, perchlorate, sulfate, nitrate, hydroxide, $BF_4^-$, $PF_6^-$, carboxylate, triflate or tosylate.

5. A process according to claim 4, wherein the anion A is chloride or acetate.

6. A process according to claim 1, wherein Y is a radical of the formula (CH$_2$)$_r$—, where r is an integer from 1 to 8, or of the formula —C(R$_5$)$_2$—(CH$_2$)$_p$—C(R$_5$)$_2$—, in which p is a number from 0 to 6 and $R_5$ is hydrogen or $C_1$–$C_4$alkyl.

7. A process according to claim 6, wherein Y is a radical of the formula —(CH$_2$)$_r$—, where r is an integer from 1 to 4, or of the formula —(CR$_5$)$_2$—(CR$_5$)$_2$—, in which $R_5$ independently at each occurrence is hydrogen or methyl.

8. A process according to claim 4, wherein halide is chloride, bromide or fluoride.

9. A process according to claim 1, wherein n and/or m is 1 and R and/or $R_1$ are as defined with the exception of nitro and COOR$_5$ and are located in position 4 of the respective benzene ring.

10. A process according to claim 1, wherein n and/or m is 1, R and/or $R_1$ are nitro or COOR$_5$ and are located in position 4 of the respective benzene ring, and $R_5$ is hydrogen or linear or branched $C_1$–$C_4$alkyl.

11. A process according to claim 1, wherein n and/or m is 2 and R and/or $R_1$ are as defined with the exception of nitro and $COOR_5$ and are located in positions 4 and 6 of the respective benzene ring.

12. A process according to claim 1, wherein n and/or m is 2 and R and/or $R_1$ are nitro or $COOR_5$ and are located in positions 3 and 5 of the respective benzene ring.

13. A process according to claim 1, wherein R and $R_1$ are nitro, $OR_5$, $COOR_5$ or $N(R_5)_2$, where $R_5$ is hydrogen or $C_1$–$C_4$alkyl.

* * * * *